United States Patent

Gür et al.

[11] Patent Number: 5,827,415
[45] Date of Patent: Oct. 27, 1998

[54] OXYGEN SENSOR

[75] Inventors: Turgut Mehmet Gür, Palo Alto, Calif.; Robert A. Huggins, Ulm, Germany

[73] Assignee: The Board of Trustees of Leland Stanford Jun. Univ., Stanford, Calif.

[21] Appl. No.: 677,171

[22] Filed: Jul. 9, 1996

Related U.S. Application Data

[63] Continuation of Ser. No. 312,115, Sep. 26, 1994, abandoned.

[51] Int. Cl.$^6$ .................................................. G01N 27/409
[52] U.S. Cl. ......................... 204/426; 73/23.31; 204/424; 204/427; 204/429; 422/83; 422/90; 422/95; 422/98
[58] Field of Search ........................... 73/23.31; 204/415, 204/424, 425, 426, 427, 428, 429; 422/83, 90, 95, 98

[56] References Cited

U.S. PATENT DOCUMENTS

| | | | |
|---|---|---|---|
| 4,096,048 | 6/1978 | Matsumoto et al. | 204/424 |
| 4,174,258 | 11/1979 | Bode | 204/424 |
| 4,208,265 | 6/1980 | Hori et al. | 204/424 |
| 4,209,377 | 6/1980 | Shinohara et al. | 204/424 |
| 4,264,425 | 4/1981 | Kimura et al. | 204/429 |
| 4,345,985 | 8/1982 | Tohda et al. | 204/425 |
| 4,347,114 | 8/1982 | Kimura et al. | 204/195 S |
| 4,407,057 | 10/1983 | Kimura et al. | 29/570 |
| 4,462,890 | 7/1984 | Touda et al. | 204/425 |
| 4,487,680 | 12/1984 | Logothetis et al. | 204/427 |
| 4,571,285 | 2/1986 | Nakazawa et al. | 204/425 |
| 4,650,560 | 3/1987 | Ueno | 204/425 |
| 4,658,790 | 4/1987 | Kitahara | 204/425 |
| 4,741,817 | 5/1988 | Croset et al. | 204/427 |
| 4,767,518 | 8/1988 | Maskalick | 204/424 |
| 4,786,476 | 11/1988 | Munakata et al. | 204/424 |
| 4,824,550 | 4/1989 | Ker et al. | 204/427 |
| 4,938,861 | 7/1990 | Kurosawa et al. | 204/425 |
| 4,961,835 | 10/1990 | Kobayashi et al. | 204/424 |
| 5,026,601 | 6/1991 | Iio et al. | 428/336 |
| 5,064,516 | 11/1991 | Rupich | 204/425 |
| 5,183,550 | 2/1993 | Mathiessen | 204/425 |
| 5,194,134 | 3/1993 | Futata et al. | 204/424 |
| 5,302,275 | 4/1994 | Dietz et al. | 204/425 |
| 5,314,605 | 5/1994 | Matthiessen | 204/415 |
| 5,320,733 | 6/1994 | Bohm | 204/415 |
| 5,360,528 | 11/1994 | Oh et al. | 204/425 |
| 5,367,283 | 11/1994 | Lauf et al. | 338/34 |
| 5,413,691 | 5/1995 | Kaneyasu et al. | 204/424 |

OTHER PUBLICATIONS

Gur, et al., Steady-State D-C Polarization Characteristics of the $O_2$, Pt/Stabilized Zirconia Interface, reprint from Journal of the Electrochemical Society, vol. 127, No. 12, Dec. 1980, pp. 2620-2628.

Gur, et al., AC Admittance Measurments on Stabilized Zirconia with Porous Platinum Electrodes, Solid State Ionics 1 (1980) pp. 251-271.

J.I. Federer, "The Effect of Reactive Gases on Oxygen Sensor Responses," J. Electrochem. Soc., vol.131, No.4, Mar. 1984, pp. 755-760.

M. Gauthier and A. Chamberland, "Solid-State Detectors for the Potentiometric Determination of Gaseous Oxides," J.Electrochem. Soc., vol.124, No.10/77, pp. 1580-1583.

(List continued on next page.)

Primary Examiner—Jill Warden
Assistant Examiner—Sharidan Carrillo
Attorney, Agent, or Firm—Flehr Hohbach Test Test Albritton & Herbert

[57] ABSTRACT

A self-contained, integrated-structure, miniature, electrochemical-type oxygen sensor is described which uses an oxygen ion conducting solid electrolyte. An encapsulated metal-metal oxide reference electrode on one surface of the solid electrolyte provides a reference oxygen pressure. A sensing electrode is placed on the other surface. The voltage developed between the reference electrode and the sensing electrode is indicative of the oxygen content of the fluid the sensing electrode is contacting.

25 Claims, 4 Drawing Sheets

OTHER PUBLICATIONS

K.Saji, H.Kondo, T.Takeuchi and I.Igarashi, "Voltage Step Characteristics of Oxygen Concentration Cell Sensors for Nonequilibrium Gas Mixtures," J.Electrochem. Soc., vol.135, No.7, Jul. 1988, pp. 1686–1691.

S.P.S.Badwal, F.T.Ciacchi, J.W.Haylock, "Nernstian behaviour of zirconia oxygen sensors incorporating composite electrodes," J. of Applied Electrochemistry, vol. 18 (1988), pp. 232–239.

K.Saji, H.Kondo, H.Takahashi, T.Takeuchi and I.Igarashi, "Influence of H2O, CO2 and various combustible gases on the characteristics of a limiting current–type oxygen sensor," J. of Applied Electrochemistry, vol. 18 (1988), pp. 757–762.

J.Fouletier, E.Mantel and M.Kleitz, "Performance characteristics of conventional oxygen gauges," Solid State Ionics, vol. 6(1982) 1–13.

H.Yamamoto, A.Asada, M. Nakazawa and H. Osanai, "Ceramic Oxygen Sensor with High Performance," Technical Digest of the 7th Sensor Symposium (1988), pp. 213–215.

H.Fukuda and T.Nagai, "Limiting Current–Type Oxygen Sensor," Technical Digest of the 7th Sensor Symposium (1988), pp. 33–36.

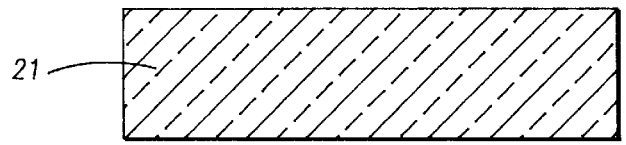
FIG.—2A
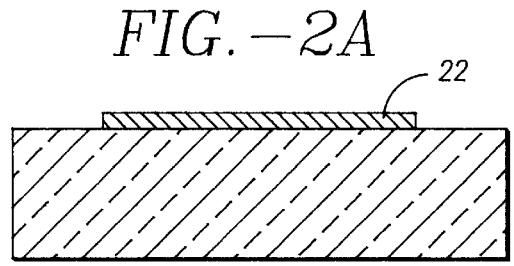
FIG.—2B
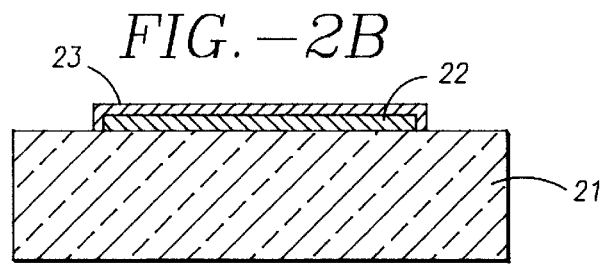
FIG.—2C
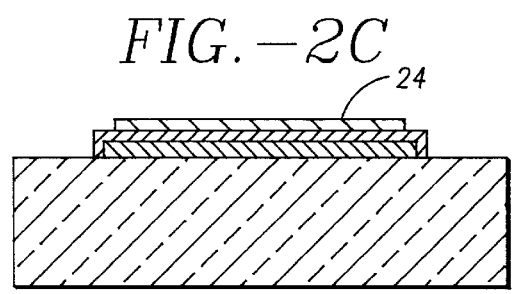
FIG.—2D
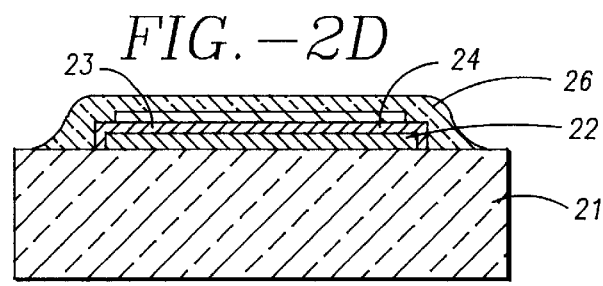
FIG.—2E
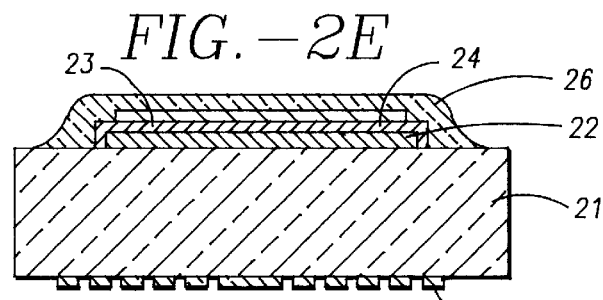
FIG.—2F

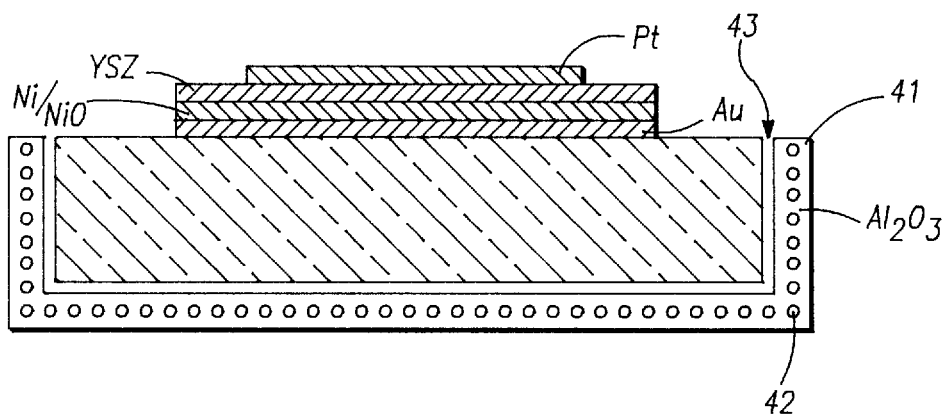
FIG.—4

OXYGEN SENSOR

This is a continuation of application Ser. No. 08/312,115 filed Sep. 26, 1994 now abandoned.

BRIEF DESCRIPTION OF THE INVENTION

This invention relates generally to an oxygen sensor, and more particularly to a miniature Nernstian type electrochemical oxygen sensor and method of manufacture.

BACKGROUND OF THE INVENTION

Zirconia ($ZrO_2$) displays considerable solid solubility (up to 20 mol percent) for many alkali and rare earth oxides at elevated temperatures. When the high temperature cubic fluorite phase of zirconia is stabilized by doping with rare earth oxides, the dopant cations substitute for the $Zr^{+4}$ sites in the crystal structure. The difference in the charge between the dopant cation and $Zr^{+4}$ gives rise to the creation of oxygen vacancies in order to maintain the charge neutrality of the crystal. Since the solubilities are high, the resulting oxygen vacancy concentrations are also high. For example, 10 mol percent CaO stabilized zirconia contains about 10 mol percent oxygen vacancies since each $Ca^{+2}$ sitting in a $Zr^{+4}$ site leads to the creation of one oxygen vacancy for charge compensation. Similarly, 10 mol percent $Y_2O_3$ stabilized zirconia contains about 5 mol percent oxygen vacancies.

Such a high vacancy concentration, approaching fractions of Avogadro's number, facilitates oxygen to selectively diffuse through this family of materials via a vacancy diffusion mechanism, hence, the high ionic conductivity and the name solid electrolyte. This high electrical conductivity remains predominantly ionic in nature even at elevated temperatures with practically no concomitant electronic conduction over a wide range of oxygen activities (e.g., from about 5 atm down to about $10^{-26}$ atm at 1000° C.).

Over the last several decades, stabilized zirconia based solid electrolytes have found extensive use in applications such as oxygen sensors, solid oxide fuel cells, oxygen pumps, electrocatalytic reactors, and electrochemically driven oxygen separation membranes. Moreover, solid state electrochemical cells employing these electrolytes have been successfully used for the determination of thermodynamic and kinetic properties of a variety of multi-component oxides. One of the most common solid oxide electrolytes used for these applications is the yttria stabilized zirconia (YSZ).

Currently, two types of high temperature electrochemical oxygen sensors are commercially available. Both types use stabilized zirconia as the oxygen ion conducting solid electrolyte. The first type is an amperometric sensor which is based on the principle of limiting current phenomenon. This device is made of a small ceramic cavity containing a 10–100 $\mu$m hole, and is hermetically sealed onto a flat solid oxide electrolyte (e.g., YSZ) slab. The dimension of the hole is critical and must be much larger than the mean free path of oxygen molecules at the sensing temperature. As increasing DC bias is applied across the electrolyte so as to remove oxygen from the ceramic cavity through the solid electrolyte, a limiting current situation is eventually reached which is governed by the rate of viscous diffusion of molecular oxygen from the environment into the cavity through the small hole. The concentration of oxygen is related linearly to the limiting current since the diffusion rate through the hole is governed by the partial pressure of oxygen in the environment outside the cavity.

This linear response sensor has two major drawbacks. First, it is good only in the moderate to high oxygen partial pressure range and generally performs poorly at low oxygen concentrations less than a few percent. Second, it is not selective only to molecular oxygen. All other oxygen containing gaseous species such as CO, $CO_2$, $H_2O$, $SO_2$, NO, etc., will contribute to the current by supplying oxygen via their respective deoxygenation reactions on the electrode surface. Thus, this type of oxygen sensor suffers considerably from interference effects from other oxygen containing constituents in the environment.

The other type of oxygen sensor is a Nernstian type electrochemical device that has two separate compartments and measures the difference between the chemical potential of oxygen on the two sides of an oxide ion conducting solid electrolyte. It is typically made of a YSZ solid electrolyte tube with suitable metal electrodes deposited on the inner, and outer walls at the closed end of the tube. This type of sensor is currently incorporated in the exhaust gas manifold of all automobiles manufactured in the Western countries. It is used for measuring the oxygen content of the exhaust gas. This information is used to control the air-to-fuel ratio for optimum combustion and engine efficiency.

The electrode reaction for oxygen incorporation into the YSZ solid electrolyte can be expressed as

  (1)

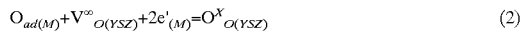  (2)

where, in accordance with Kröger-Vink notation, $V_O^{\bullet\bullet}$ denotes an oxygen vacancy in YSZ with an effective charge of +2 with respect to the perfect lattice, $O^x{}_O$ is neutral oxygen occupying a normal oxygen lattice site in YSZ, $O_{2(g)}$ is molecular oxygen in the gas phase, $O_{ad(M)}$ is adsorbed oxygen atoms on the metal electrode surface, and $e'_{(M)}$ is an electron with an effective charge of –1, residing in the metal electrode (M). Eq. (1) represents the dissociative adsorption of molecular oxygen on the metal electrode surface. The adsorbed oxygen picks up two electrons from the metal electrode and is incorporated into the zirconia as a neutral species.

The oxygen activity, $a_{O2}$, is related to the open circuit potential, E, by the Nernst equation:

$$E = -RT/4F \ln(a'_{O_2}/a''_{O_2}) \quad (3)$$

where R is the universal gas constant, T denotes the temperature, and the superscripts indicate different oxygen activities on each side of the electrolyte.

Assuming that ideal gas behavior is obeyed at these elevated temperatures and the oxygen activity on one side of the electrolyte can be fixed by using a suitable reference, Eq. (3) can be expressed as $$E = -RT/4F \ln(P_{O_2}/P_{refO_2}) \quad (4)$$

where $P_{refO2}$ is the reference oxygen pressure on one side of the electrolyte (e.g., for air, $P_{refO2}$=0.21 atm) and $P_{o2}$ denotes the unknown oxygen pressure on the other side. Eq. (4), in fact, represents the principle under which Nernstian type oxygen sensors operate.

Presently, all commercial Nernstian type oxygen sensors have a two-compartment tubular design where one surface of the tube is exposed to air to serve as the reference electrode for fixed and known oxygen activity. The other surface of the tube sensor is usually exposed to the environment with the unknown oxygen activity. These two-compartment sensors are bulky, prone to frequent thermal and mechanical failure, and require gas-tight separation between the oxygen reference electrode compartment and the environment of interest. Any oxygen leak between the two compartments short circuit the oxygen chemical potential difference and adversely affect the accuracy and the reliability of the sensor. Their large size as well as other considerations usually make this design unsuitable for monitoring the oxygen content in many controlled environments and applications (e.g., thin film deposition).

This disclosure teaches a novel, self-contained, integrated structure oxygen sensing device. Two closely related but distinct designs are described for this sensor. Both designs operate on the Nernstian principle, i.e., they are electrochemical sensing devices. They are suitable for process control and monitoring of oxygen in many different environments including deposition and synthesis systems that operate under a wide range of pressures and/or controlled atmospheres, in situ monitoring of oxygen in streaming and flue gases, in molten metals and alloys, in steel-making and other metal foundry operations, in combustion processes, in medical applications and devices, in air management systems, in electronic circuits and hermetically sealed chips, in process control in electronic, metallurgical, chemical, and petrochemical industries.

OBJECTS AND SUMMARY OF THE INVENTION

It is an object of the invention to provide an integrated structure electrochemical oxygen sensor.

It is another object of the invention to provide a Nernstian type electrochemical oxygen sensor that has a self-contained metal-metal oxide oxygen reference electrode.

It is a further object of the invention to provide a miniature integrated structure electrochemical oxygen sensor.

It is another object of the invention to provide a method of manufacture of an electrochemical oxygen sensor which employs microelectronic thin film technology.

The foregoing and other objects of the invention are achieved by an oxygen sensor which includes a thin ion conducting solid electrolyte, a sealed metal-metal oxide film applied to one surface of the solid electrolyte serving as a reference electrode, an oxygen barrier layer to encapsulate the reference electrode, and a sensing electrode on the other surface of the thin solid electrolyte.

BRIEF DESCRIPTION OF THE DRAWINGS

The invention will be more clearly understood from the following description when it is read in conjunction with the accompanying drawings, wherein:

FIGS. 2A–2F show the steps in fabricating the device shown in FIG. 1;

FIG. 4 is a schematic sectional view of a Nernstian type oxygen sensor supported by a heater assembly;

DESCRIPTION OF PREFERRED EMBODIMENT(S)

Figure 1:
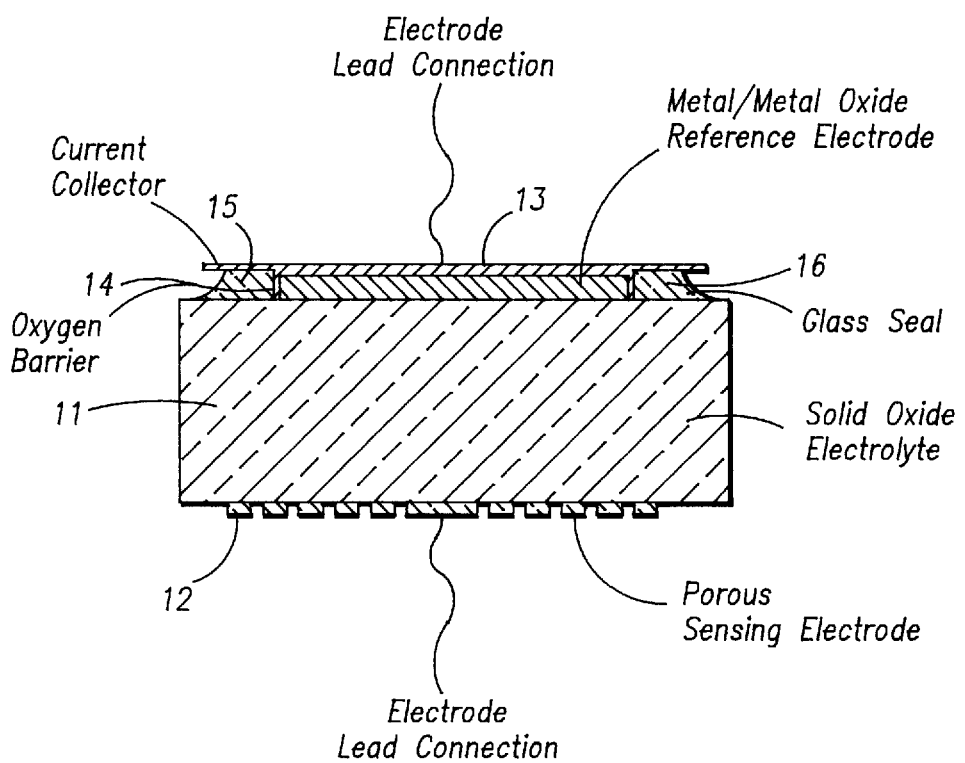
FIG. 1 is a schematic sectional view a Nernstian type oxygen sensor in accordance with one embodiment of the invention.

The sensor shown in FIG. 1 is made of a thin solid electrolyte slab or body 11, preferably $Y_2O_3$ stabilized zirconia (YSZ). The slab can be less than 1 millimeter in thickness. One of the faces of the YSZ slab 11 is coated with a thin porous layer 12, such as Pt, Ag, or a perovskite. The layer 12 serves as the sensing electrode of the sensor and is in contact with the environment having the unknown oxygen content.

A metal-metal oxide binary mixture 13 is disposed on the opposite face of the slab to serve as the reference electrode. One way of forming the metal-metal oxide binary mixture is to coat this face with a thin layer of a metal such as Ni, Cu, or Cr. Various suitable deposition techniques such as sputtering, evaporation, spraying, screening, etc., can be used for this purpose. This metal layer is then fully oxidized to the metal oxide. Another way of providing the oxide layer is to directly deposit the metal oxide on the face of the electrolyte by using one of the deposition techniques described above. The metal oxide layer is then encapsulated by a thick Au coating 14 that serves as an oxygen barrier layer. The metal oxide is then partially reduced under electrochemically controlled conditions to obtain the metal-metal oxide binary mixture. This can be achieved by applying a suitably small DC current from an external power source and partially titrate the oxygen out of the metal oxide through the YSZ electrolyte. The intent is to reduce part of the oxide to metal and form the two phase metal-metal oxide mixture. The resulting metal-metal oxide two phase mixture serves as the self-contained oxygen reference electrode. It is encapsulated and completely isolated from the ambient oxygen environment by the Au barrier layer.

Another way to make an oxygen reference electrode is to use a pressed thin pellet of a metal-metal oxide powder mixture placed in good physical contact with the surface of the YSZ electrolyte. Again, all external surfaces of the pressed pellet are coated with thick oxygen barrier layer 14. A Pt foil current collector 15 is pressed against the top of the oxygen barrier layer 14. The current collector 15 is then covered with a thick layer of a glass slurry and fired to consolidate and form a glass capsule 16.

In the case where the chosen metal-metal oxide reference electrode system is chemically reactive towards the solid oxide electrolyte of choice, it is advisable to physically separate the two by depositing a thin porous interlayer of Pt, Ag, or Au between the solid oxide electrolyte and the metal-metal oxide reference electrode. The presence of such an interlayer may even enhance the rate of the charge transfer reaction at this interphase, and contribute to faster response time for the sensor.

The sensor is provided with a suitable heater, not shown in FIG. 1, to maintain an operating temperature of 500°–800° C. Operation at lower or higher temperatures is also possible. The heater can be in the form of a resistive coil, thick film, or sheet heater. A suitable thermocouple attachment is made to the sensor for accurate temperature monitoring.

The finished size of the sensor may be as small as five millimeters in the largest dimension. There are obvious advantages to having such small dimensions. For example, providing heat to the sensor element does not present practical problems. The susceptibility to failure due to thermal and mechanical shock is drastically reduced. For process control during thin film deposition and other synthesis or analytical diagnostic applications, small size is less disruptive to other processing parameters and conditions, so the sensor can be installed as close to the substrate as physically possible.

A key feature of this novel sensor is that it contains its own oxygen reference electrode made of a suitable metal-metal oxide mixture that is sufficiently electronically conductive. The Gibbs phase rule dictates that the two-phase, metal-metal oxide binary equilibria fixes the oxygen activity at a given temperature. Hence, this fixed and known oxygen activity can be used as the oxygen reference and the unknown oxygen content can be obtained from Eq. (4).

Another feature is the manner the metal-metal oxide reference electrode, is encapsulated and completely isolated from any contact with oxygen in the environment. For the reliable and accurate performance of this novel sensor, it is imperative that the metal-metal oxide reference electrode does not exchange oxygen with the environment. Hence, it needs to be sealed off carefully from the environment. One component of the seal is the oxygen barrier layer, preferably Au, that serves as a diffusion barrier for oxygen. A suitable glass, such as Pyrex, which has a favorable softening point in the desired sensing temperature range constitutes the second component of the seal. The oxygen barrier layer also prevents any possible chemical reaction between the metal-metal oxide reference electrode and the glass seal.

FIGS. 2A–2F show one method of forming sensors in accordance with the invention. A thin wafer or slab 21 of solid electrolyte is processed to form sensors. The description to follow describes the fabrication of a single electrochemical oxygen sensor. It will be apparent that a larger wafer can be used and that by suitable masking and processing similar to those used in microelectronic thin film technology a plurality of devices can be formed on a slab during one process. The slab can then be diced to form individual sensors. Preferably, the solid oxide electrolyte is $Y_2O_3$ stabilized zirconia. However, there are other suitable electrolytes such as other zirconia-based solid solutions, hafnia-based solid solutions, ceria-based solid solutions, thoria-based solid solutions, urania-based solid solutions, bismuth oxide-based solid solutions and oxygen saturated fluorides. A listing of suitable solid electrolytes is set out hereinafter. A metal layer 22 which can be oxidized and processed to form a metal-metal oxide mixture is formed on one major surface of the slab, FIG. 2B. The metal layer may be deposited by suitable deposition techniques such as sputtering, evaporation, spraying, screening, etc. The layer is fully oxidized to form a metal oxide. Preferable metals are Fe, Co, Ni, Cu, and W, which form metal-metal oxide layers Fe/FeO, Co/CoO, Ni/NiO, $Cu/Cu_2O$ and $W/WO_3$, respectively. Other reference electrodes are suitable depending upon the temperature at which the oxygen sensor is to be operated. A partial list of suitable metal-metal oxide reference electrodes is presented hereinafter.

The oxide layer 22 is encapsulated with a thick Au or Pt coating or film that serves as an oxygen barrier layer 23, FIG. 2C. A suitable, oxidation-resistant current collector 24 such as platinum foil is formed on the top of the oxygen barrier film, FIG. 2D. The barrier film and the current collector are then covered with a thick layer of a glass slurry and fired to consolidate the slurry and form a glass capsule 26, FIG. 2E. The metal oxide is then partially reduced under electrochemically controlled conditions, previously described, to obtain the metal-metal oxide binary mixture. This conversion can be achieved by applying a suitably small DC current from an external power source and partially titrating the oxygen out of the metal oxide through the solid electrolyte. The intent is to reduce part of the oxide to metal and form the two-phase metal-metal oxide mixture. The resulting metal-metal oxide, two-phase mixture then serves as the self-contained oxygen reference electrode that is encapsulated and completely isolated from the ambient oxygen environment by the gold barrier layer. The next step in the process is to apply a porous layer 27 of platinum, silver or a perovskite material which serves as the sensing electrode and which is placed in direct communication with the environment whose oxygen content is to be measured.

In a still more advanced design of the sensor, all components of the sensor including the YSZ solid electrolyte may be deposited as a thin film using chemical or physical vapor deposition techniques. This provides an opportunity for the entire sensor, including the electrodes and the electrode leads, to be made by using thin film deposition technology to fabricate micron size on-chip or stand-alone oxygen sensors that may have a wide range of electronics, process control, and other applications. One other important aspect of this thin film design is that, due to the solid electrolyte film that can be deposited as thin as 10 nm, this sensor may be suitable for sensing oxygen at temperatures much lower than can possibly be attained presently with similar sensors based on solid oxide electrolytes.

Figure 3:
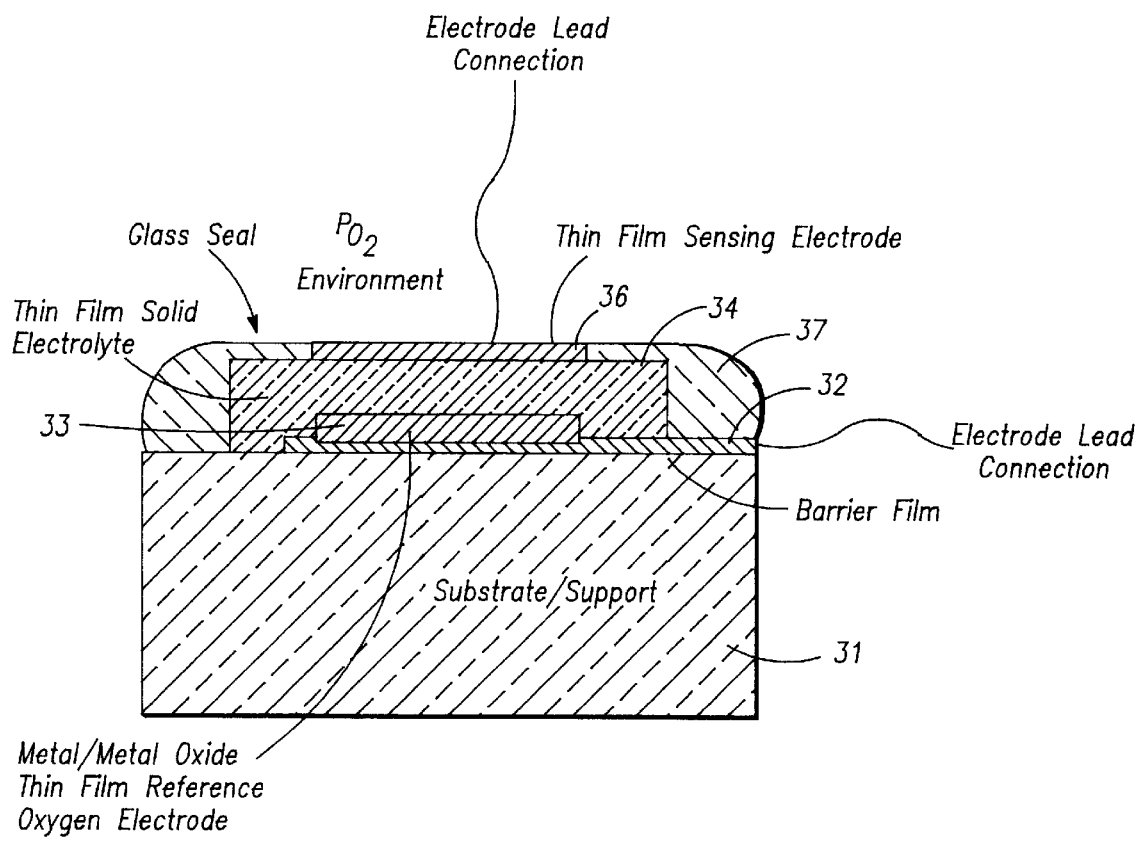
FIG. 3 is a schematic sectional view of a another Nernstian type oxygen sensor.

This thin film design, which may be as small as a few micrometers in each final dimension, is illustrated in FIG. 3. In the case of a stand-alone sensor, a substrate material 31, which may also serve as mechanical support, is coated with a nonporous, oxygen impervious barrier layer 32, such as gold. The substrate material may be an electronically insulating ceramic such as alumina, stabilized zirconia or silica, or electronically insulating thin layers of a suitable material on a substrate such as silicon. It is important that the barrier layer is chemically inert to the substrate material. This barrier layer may or may not be necessary, depending on the choice of substrate and reference electrode materials. If these materials are chemically reactive towards each other or make alloys at the operating temperature of the sensor, then a barrier layer is necessary in order to prevent chemical reaction between the reference electrode and the substrate. The geometric boundary of the barrier layer, which may be as small as a few micrometer squares or as large as a few millimeter squares, is extended beyond the boundaries of the reference electrode 33, as shown in FIG. 2, such that a lead can be attached to the barrier layer which also serves as a voltage sensing electrode.

The reference electrode 33 comprises a metal and its oxide suitable to serve as an oxygen reference electrode. The metal and metal oxide can be deposited separately or jointly as a thin film, possibly 100 to 1000 nm thick. If only a metal layer is deposited, the procedure to form the metal-metal oxide mixture in situ, described above, can be. followed. A 10–1000 nm thick solid oxide electrolyte layer 34 is deposited over the metal-metal oxide reference electrode layer. The thickness and hence the resistance of the solid oxide electrolyte layer greatly influences the operating temperature and the response time of the sensor. Accordingly, this thickness can be tailored as desired. Naturally, thinner electrolyte layers allow the sensor faster response times and lower operating temperatures, and vice versa.

It is essential that the reference electrode layer be completely isolated from the oxygen ambient. Hence, it is preferable to deposit the oxide layer 34 larger in area than the underlying reference electrode layer, such that the reference electrode is completely encapsulated. The 100–1000 nm thick porous sensing electrode 36 is deposited on top of the solid electrolyte layer to complete the thin film stack. In order to enforce and improve the isolation of the reference electrode from the oxygen ambient, a layer of glass 37 is formed around the periphery of the sensor stack. The electrode lead connections are attached to the sensing electrode as well as the barrier layer as mentioned earlier. The leads are connected to a voltage sensing device.

The sensors may be supported or housed in a suitable heating device if they are to be used as stand-alone sensors. An example of a suitable heater is shown in FIG. 4 for supporting a device of the type described with reference to FIG. 3. The device is placed in a cup-shaped holder 41 formed of insulating material such as $Al_2O_3$. A heating element 42 is embedded in the insulating material. It is apparent that other modes of heating can be employed such as thin film heaters. The operating temperature of the sensor is continuously monitored by a temperature sensor such as a thermocouple 43. This operating temperature fixes the oxygen activity (i.e., the oxygen partial pressure) of the encapsulated metal-metal oxide reference electrode. The voltage difference measured across the electrode leads (V), the oxygen reference activity ($P_{refO2}$), and the operating temperature (T), used in the Nernst equation (Eq. (4)) yields the unknown oxygen activity (i.e., the partial pressure ($P_{O2}$) of the ambient).

Although electrochemical oxygen sensor has been described with reference to preferred solid electrolyte materials, metal-metal oxide materials, sensing electrode materials, oxygen barrier materials and encapsulation glass it can be constructed with other materials.

The following are examples of such other solid electrolyte materials, metal-metal oxide reference materials, sensing electrode materials, oxygen barrier materials and encapsulating materials.

Solid Electrolyte Materials
Zirconia Based Solid Solutions
$ZrO_2$—MO where M=Mg, Ca, Sr, Ba
$ZrO_2$—$M_2O_3$ where M=Sc, Y, La, Pr, Nd, Sm, Gd, Tb, Dy, Ho, Er, Tm, Yb, Lu
$ZrO_2$—$Bi_2O_3$—$M_2O_3$ where M=Sc, Y, La, Pr, Nd, Sm, Gd, Tb, Dy, Ho, Er, Tm, Yb, Lu
Hafnia Based Solid Solutions
$HfO_2$—MO where M=Mg, Ca, Sr, Ba
$HfO_2$—$M_2O_3$ where M=Sc, Y, La, Pr, Nd, Sm, Gd, Tb, Dy, Ho, Er, Tm, Yb, Lu
Ceria Based Solid Solutions
$CeO_2$—MO where M=Mg, Ca, Sr, Ba
$CeO_2$—$M_2O_3$ where M=Sc, Y, La, Pr, Nd, Sm, Gd, Tb, Dy, Ho, Er, Tm, Yb, Lu
Thoria Based Solid Solutions
$ThO_2$—MO where M=Mg, Ca, Sr, Ba
$ThO_2$—$M_2O_3$ where M=Sc, Y, La, Pr, Nd, Sm, Gd, Tb, Dy, Ho, Er, Tm, Yb, Lu
Urania Based Solid Solutions
$UO_2$—MO where M=Mg, Ca, Sr, Ba
$UO_2$—$M_2O_3$ where M=Sc, Y, La, Pr, Nd, Sm, Gd, Tb, Dy, Ho, Er, Tm, Yb, Lu
Bismuth Oxide Based Solid Solutions
$Bi_2O_3$—MO where M=Mg, Ca, Sr, Ba, Pb
$Bi_2O_3$—$M_2O_3$ where M=Sc, Cr, Y, Mo, Tb, Er, Yb,
$Bi_2O_3$—$WO_3$
$Bi_2O_3 \cdot (PbO)_{1-x} \cdot (CaO)_x$
Oxygen Saturated Fluorides
$CaF_2$—CaO
$BaF_2$—BaO Metal/Metal Oxide Reference Electrode Materials
Preferred Reference Electrode Materials
Fe/FeO, Co/CoO, Ni/NiO, Cu/$Cu_2O$, W/$WO_3$
Other reference electrode materials that may be suitable depending on the operating temperature of the sensor:
Ti/TiO, V/VO, Cr/$Cr_2O_3$, Mn/MnO, Zn/ZnO, Nb/NbO, Mo/$MoO_2$, Ru/RuO, Rh/RhO, Pd/PdO, Ag/$Ag_2O$, Cd/CdO, In/$In_2O_3$, Sn/SnO, Sb/$Sb_2O_3$, Te/$TeO_2$, Ta/$Ta_2O_5$, Re/ReO, Os/OsO, Ir/IrO, Pt/PtO, Tl/$Tl_2O_3$, Pb/PbO The following table gives the equilibrium oxygen pressure, $P_{O2}$, for selected metal-metal oxide reference electrode materials at 1000K.

| | |
|---|---|
| Cu/$Cu_2O$ | $1.049 \times 10^{-10}$ atm |
| Ni/NiO | $2.564 \times 10^{-16}$ atm |
| Co/CoO | $8.804 \times 10^{-18}$ atm |
| W/$WO_3$ | $4.053 \times 10^{-21}$ atm |
| Mo/$MoO_2$ | $6.660 \times 10^{-22}$ atm |
| Fe/FeO | $2.392 \times 10^{-22}$ atm |
| Cr/$Cr_2O_3$ | $5.371 \times 10^{-31}$ atm |
| Nb/NbO | $4.668 \times 10^{-35}$ atm |
| V/VO | $1.215 \times 10^{-36}$ atm |
| Zr/$ZrO_2$(**) | $3.739 \times 10^{-48}$ atm |

(**)The equilibrium oxygen pressure for Zr/$ZrO_2$ is given for comparison purposes. When a reference electrode is chosen, it is important that the equilibrium oxygen pressure should not be lower than that corresponding to the decomposition oxygen pressure of the electrolyte used, say, the Zr/$ZrO_2$ equilibrium in case of the zirconia based electrolytes. Otherwise, the electrolyte will decompose under the reducing oxygen pressure and the sensor will eventually fail.

Sensing Electrode Materials

Metals: Pt, Ag, Au, Pd, Ir, Rh, Re, Os, and their alloys
Cermets: Pt—$ZrO_2$, Pd—$ZrO_2$, Ag—Pd—$ZrO_2$ cermet
Undoped Perovskites With General Formula
$LaMO_3$ where M=V, Cr, Mn, Fe, Co, Ni
A-Site Doped Perovskites With General Formula
$La_{1-x}M_xNO_3$ where M=Ca, Sr, Ba; and N=Cr, Mn, Fe, Co, Ni
A- and B-Site Doped Perovskites With General Formula
$AM_{1-x}N_xO_3$ where A=Ca, Sr, Ba; M=Cr, Mn, Fe, Co, Ni; and N=Cr, Mn, Fe, Co, Ni; such that the elements chosen for M and N are different from each other for each compound.

Oxygen Barrier Materials

Au, Pt, Ta, Mo, W, Nb, Zr, NbN, ZrN, TiN, AlN, $(Tl_{1-x}Al_x)$N, $Si_3N_4$

Encapsulating Materials

Borosilicate glass, soda glass, aluminum and magnesium silicate based glasses, phosphate glasses Thus, there has been provided a novel, self-contained Nernstian-type, miniature electrochemical oxygen sensor which uses an oxygen ion conducting solid electrode and one encapsulated metal-metal oxide reference electrode.

What is claimed:

1. A Nernstian type oxygen sensor comprising:
   an ion conducting solid electrolyte member having a spaced major surfaces;
   a reference electrode for providing a reference oxygen level comprising a layer of metal-metal oxide on a first major surface of the solid electrolyte member;
   an oxygen barrier layer in direct contact with all exposed surfaces of said reference electrode to encapsulate the metal-metal oxide layer and completely isolate the layer from oxygen in the environment whereby the oxygen in the environment does not change the reference oxygen level, said barrier layer making electrical contact to the metal-metal oxide layer of said reference electrode; and
   a sensing electrode on a second major surface of the electrolyte in direct contact with the environment having unknown oxygen content, said sensing electrode dissociatively adsorbing molecular oxygen on a surface of the sensing electrode whereby an open circuit voltage developed between said metal-metal oxide layer of the reference electrode and the sensing electrode is indicative of the unknown oxygen content in the environment.

2. An oxygen sensor as in claim 1 in which the ion conducting solid electrolyte member comprises $Y_2O_3$ stabilized zirconia.

3. An oxygen sensor as in claim 1 in which the ion conducting solid electrolyte member is selected from the group consisting of zirconia based solid solutions, hafnia-based solid solutions, ceria based solid solutions, thoria-based solid solutions, urania-based solid solutions, bismuth oxide based solid solutions and oxygen saturated fluorides.

4. An oxygen sensor as in claim 1 in which the reference electrode metal-metal oxide layer is selected from the group consisting of Fe/FeO, Co/CoO, Ni/NiO, $Cu/Cu_2O$ and $W/WO_3$, $Mo/MoO_2$, $Cr/Cr_2O_3$, Nb/NbO and V/Vo.

5. An oxygen sensor as in claim 4 in which the metal-metal oxide layer has an oxygen pressure higher than a decomposition oxygen pressure of the solid electrolyte member, whereby the solid electrolyte will not decompose.

6. An oxygen sensor as in claim 2 in which the reference electrode metal-metal oxide layer is selected from the group consisting of Fe/FeO, Co/CoO, Ni/NiO, $Cu/Cu_2O$ and $W/WO_3$, $Mo/MoO_2$, $Cr/Cr_2O_3$, Nb/NbO and V/Vo.

7. An oxygen sensor as in claim 3 in which the reference electrode metal-metal oxide layer is selected from the group consisting of Fe/FeO, Co/CoO, Ni/NiO, $Cu/Cu_2O$ and $W/WO_3$, $Mo/MoO_2$, $Cr/Cr_2O_3$, Nb/NbO and V/Vo.

8. An oxygen sensor as in claim 1 in which the oxygen barrier layer is gold or platinum.

9. An oxygen sensor as in claim 4 in which the oxygen barrier layer is selected from the group consisting of Au, Pt, Ta, Mo, W, Nb, Zr, NbN, ZrN, TiN, AlN, $(Ti_{1-x}Al_x)N$, $Si_3N_4$.

10. An oxygen sensor as in claim 2 in which the oxygen barrier layer is gold or platinum.

11. An oxygen sensor as in claim 3 in which the oxygen barrier layer is gold or platinum.

12. An oxygen sensor as in claim 3 in which the oxygen barrier layer is selected from the group consisting of Au, Pt, Ta, Mo, W, Nb, Zr, NbN, ZrN, TiN, AlN, $(Ti_{1-x}Al_x)N$, $Si_3N_4$.

13. An oxygen sensor as in claim 4 in which the oxygen barrier layer is gold or platinum.

14. An oxygen sensor as in claim 4 in which the oxygen barrier layer is selected from the group consisting of Au, Pt, Ta, Mo, W, Nb, Zr, NbN, ZrN, TiN, AlN, $(Ti_{1-x}Al_x)N$, $Si_3N_4$.

15. An oxygen sensor as in claim 1 in which the sensing electrode is a metal.

16. An oxygen sensor as in claim 1 in which the sensing electrode is selected from metals, cermets, and perovskites.

17. An oxygen sensor as in claim 3 in which the sensing electrode is a metal.

18. An oxygen sensor as in claim 1 in which the sensing electrode is selected from metals, cermets, and perovskites.

19. An oxygen sensor as in claim 4 in which the sensing electrode is a metal.

20. An oxygen sensor as in claim 4 in which the sensing electrode is selected from metals, cermets, and perovskites.

21. An oxygen sensor as in claim 1 in which the reference electrode including the metal-metal oxide layer and the barrier layer are encapsulated in a glass layer.

22. An oxygen sensor as in claim 2 in which the reference electrode and the oxygen barrier layer are encapsulated in glass layer.

23. A Nernstian type oxygen sensor comprising:

an ion conducting solid electrolyte member having spaced major surfaces;

a reference electrode for providing a reference oxygen level comprising a layer of metal-metal oxide on a first major surface of the solid electrolyte member;

a thin porous metal-metal oxide layer disposed between said electrolyte and said layer to prevent reaction between the reference electrode and the electrolyte member;

an oxygen barrier layer in direct contact with all exposed surfaces of said reference electrode to encapsulate said metal-metal oxide layer and isolate the layer from oxygen in the environment whereby oxygen in the environment does not change the reference oxygen level; and a porous sensing electrode on a second major surface of the electrolyte in direct contact with the environment having an unknown oxygen concentration, said sensing electrode dissociatively adsorbing molecular oxygen from the environment on a surface of the sensing electrode whereby an open circuit voltage developed between said sensing electrode and the metal-metal oxide layer of the reference electrode is indicative of the molecular oxygen concentration in the environment.

24. An oxygen sensor as in claim 23 in which said reference electrode and barrier layer are encapsulated in glass.

25. An oxygen sensor as in claim 23 which is less than five millimeters in its largest dimension.

\* \* \* \* \*